(12) United States Patent
Franke et al.

(10) Patent No.: US 9,119,966 B2
(45) Date of Patent: Sep. 1, 2015

(54) SYSTEMS AND METHODS THAT PROVIDE AN ELECTRICAL WAVEFORM FOR NEURAL STIMULATION OR NERVE BLOCK

(71) Applicant: Case Western Reserve University, Cleveland, OH (US)

(72) Inventors: Manfred Franke, Cleveland, OH (US); Kevin L. Kilgore, Avon Lake, OH (US); Niloy Bhadra, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 14/275,822

(22) Filed: May 12, 2014

(65) Prior Publication Data

US 2014/0336728 A1    Nov. 13, 2014

Related U.S. Application Data

(60) Provisional application No. 61/821,873, filed on May 10, 2013, provisional application No. 61/824,525, filed on May 17, 2013.

(51) Int. Cl.
*A61N 1/375* (2006.01)
*A61N 1/08* (2006.01)
*A61N 1/36* (2006.01)
*A61N 1/378* (2006.01)

(52) U.S. Cl.
CPC ........ *A61N 1/36142* (2013.01); *A61N 1/36125* (2013.01); *A61N 1/3782* (2013.01)

(58) Field of Classification Search
None
See application file for complete search history.

(56) References Cited

U.S. PATENT DOCUMENTS

2009/0157147 A1\* 6/2009 Cauller et al. .................. 607/61

\* cited by examiner

*Primary Examiner* — Brian T Gedeon
(74) *Attorney, Agent, or Firm* — Tarolli, Sundheim, Covell & Tummino LLP

(57) ABSTRACT

One aspect of the present disclosure relates to a system that can provide an electric waveform for neural stimulation or nerve block. The system can include a first circuit component configured to provide a self-oscillating, voltage-boosted electric waveform. In some instances, the first circuit component can provide a "pause" waveform (e.g., with a period (T) that includes a swing time (ts) in which the waveform varies in a biphasic manner and a pause time (tp) in which the waveform has a constant amplitude). The system can also include a second circuit component configured to ensure that the oscillating signal is charge-balanced across at least one period of the self-oscillating, voltage-boosted electric waveform.

11 Claims, 11 Drawing Sheets

SYSTEMS AND METHODS THAT PROVIDE AN ELECTRICAL WAVEFORM FOR NEURAL STIMULATION OR NERVE BLOCK

RELATED APPLICATIONS

This application claims the benefit of U.S. Provisional Application No. 61/821,873, filed May 10, 2013, entitled "LC-BLOCKING-AND-DC-BALANCING CIRCUIT." This application also claims the benefit of U.S. Provisional Application No. 61/824,525, filed May 17, 2013, entitled "BALANCED ELECTRODE SYSTEM." These provisional applications are hereby incorporated by reference in their entireties for all purposes.

TECHNICAL FIELD

The present disclosure relates generally to neural stimulation and nerve block and, more specifically, to systems and methods that can provide an electrical waveform that can be used for neural stimulation or nerve block.

BACKGROUND

High frequency alternating current waveforms in the kilohertz range (KHFAC waveforms) can provide nerve block (e.g., to control pain and/or spasticity). For example, the nerve block can be immediate, partial, selective, complete, and/or fully reversible. However, many stimulators that can provide KHFAC waveforms are impractical or impossible to incorporate in an implantable neural prosthesis devices. These stimulators require a large, heavy battery that is impractical for an implantable device. Additionally, if any portion of the stimulator were to experience an electric failure, such as open circuit or a short circuit, the stimulator could provide a continuous supply of direct currents (DC) to the stimulation electrode of the neural prosthesis, potentially damaging the electrode and/or the nerve.

SUMMARY

The present disclosure relates generally to neural stimulation and nerve block and, more specifically, to systems and methods that can provide an electrical waveform that can be used for neural stimulation or nerve block. For example, the systems and methods described herein can be easily incorporated into an implantable neural prosthesis devices for neural stimulation or nerve block.

In one aspect, the present disclosure can include a system that provides an electric waveform for neural stimulation or nerve block. The system can include a first circuit component that can be configured to provide a self-oscillating, voltage-boosted electric waveform. The system can also include a second circuit component configured to ensure that the self-oscillating, voltage-boosted electric signal is charge-balanced across a period of the oscillating electric waveform.

In another aspect, the present disclosure can include a method for providing a waveform for neural stimulation or nerve block. The method can include the step of generating a biphasic waveform characterized by an amplitude that varies biphasicly and configured for neural stimulation or nerve block. For example, the biphasic waveform can be provided by a waveform generator device. The method can also include the step of interrupting the biphasic waveform for a pause time, wherein the interrupted waveform comprises a substantially constant amplitude. For example, the interrupting can be accomplished by a switch coupled to the waveform generator device.

In a further aspect, the present disclosure can include a waveform generation device configured to provide an electric waveform for neural stimulation or nerve block. The waveform generation device can include a first circuit component that can be configured to provide a self-oscillating, voltage-boosted electric waveform. The waveform generation device can also include a second circuit component can be configured to output the self-oscillating, voltage-boosted electric waveform that is charge-balanced across at least one period of the oscillating electric waveform. The waveform generation device can also include a switch coupled to the first circuit component or the second circuit component. The switch can be configured to short-circuit an output of the self-oscillating, voltage-boosted electric waveform during a pause time interval (e.g., to discharge contaminating noise).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
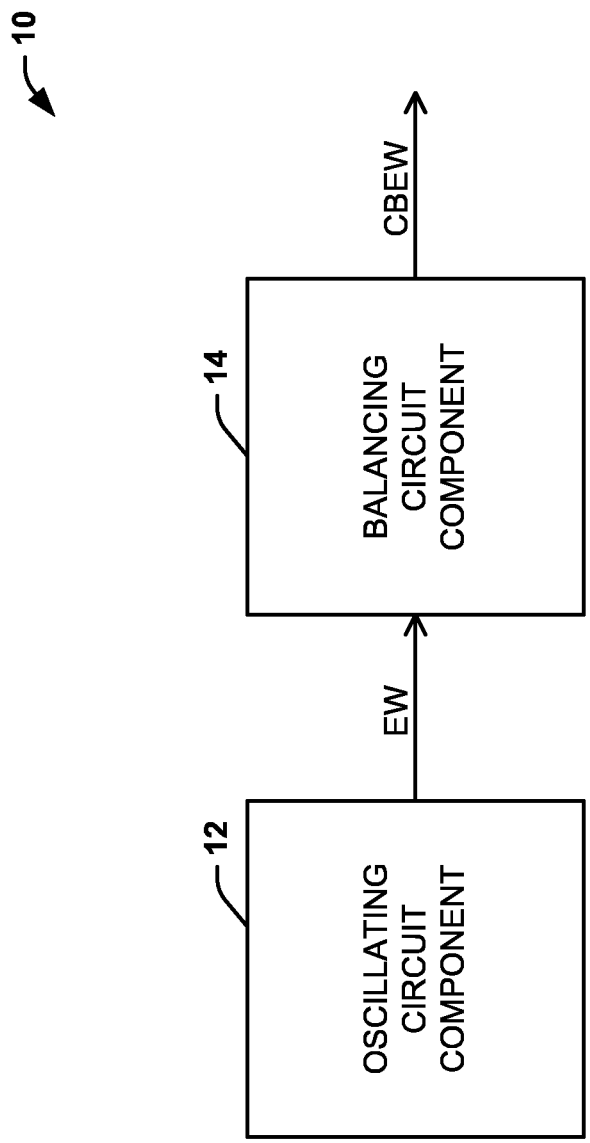
FIG. 1 is a schematic block diagram showing a system that can provide an electric waveform for neural stimulation or nerve block, in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "neural prosthesis" or "neural prosthetic" can refer to one or more devices that can substitute for a neurological function (e.g., motor function, sensory function, cognitive function, etc.) that has been damaged (e.g., as a result of a neurological disorder). For example, a neural prosthesis can include a stimulation device that restores neurological function ("neural stimulation") and/or a blocking device that blocks nerve conduction ("nerve block"). The term "stimulation waveform," as used herein, can encompass an electrical waveform used for neural stimulation and an electrical waveform used for nerve block.

As used herein, the term "nerve" can refer to a "peripheral nerve." Generally, a peripheral nerve can refer to a nerve in a patient's body other than brain and spinal cord. A peripheral nerve can include a bundle of fibers (including motor and sensory fibers) that can connect the brain and spinal cord to the rest of the patient's body. For example, a peripheral nerve can control the functions of sensation, movement, and motor coordination. In some instances, the peripheral nerve can conduct information bi-directionally (e.g., providing both motor control and sensory feedback).

As used herein, the term "electric waveform" can refer to an electrical signal that can be generated by a waveform generator and applied to the nerve with an electrode to achieve neural stimulation or nerve block. In some instances, the electrical waveform can be a mathematical description of a change in voltage over time (or "voltage controlled") or a change in current over time (or "current controlled"). In some instances, the electric waveform can be a biphasic waveform. The terms "electric waveform," "stimulation waveform," "waveform," and "signal" can be used interchangeably herein.

As used herein, the term "biphasic waveform" can refer to an electric waveform that includes both an anodic phase of the waveform and a cathodic phase. The anodic phase and the cathodic phase can be applied in either order. Examples of biphasic waveforms can include a pulsed waveform, a sinusoidal waveform, a near sinusoidal waveform, a high frequency electric alternating current (KHFAC) waveform (e.g., in the kilohertz frequency range), a charge-balanced direct current (CBDC) waveform, or a multi-phased direct current (MPDC) waveform.

As used herein, the term "substantially constant" can refer to a complete (e.g., 100%) or partial (e.g., less than 100%, such as about 90%, about 80%, about 70%, about 60%, or less than about 50%) constant amplitude electric waveform. Unless indicated otherwise, the terms "substantially constant" and "constant" can be used interchangeably herein.

As used herein, the term "medical professional" can refer to can refer to any person involved in medical care of a patient including, but not limited to, physicians, medical students, nurse practitioners, nurses, and technicians.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview.

The present disclosure relates generally to neural stimulation and nerve block and, more specifically, to systems and methods that can provide an electrical waveform that can be used for neural stimulation or nerve block. For example, the systems and methods described herein can be easily incorporated into an implantable neural prosthesis devices for neural stimulation or nerve block. For example, a system as described herein can operate on a very low supply voltage (e.g., 0 Volts-9 Volts), allowing the circuit to run longer on smaller implanted batteries.

In some instances, a system can provide an electric waveform for neural stimulation or nerve block. The system can include a first circuit component configured to provide a self-oscillating, voltage-boosted electric waveform. The system can also include a second circuit component configured to ensure that the oscillating signal is charge-balanced across a period of the self-oscillating, voltage-boosted electric waveform.

III. Systems

One aspect of the present disclosure can include a system that can that can provide an electric waveform for neural stimulation or nerve block. In some instances, the electric waveform can be a charge-balanced, biphasic waveform. For example, the charge-balanced, biphasic waveform can be self-oscillating and voltage-boosted.

As shown in FIG. 1, one aspect of the present disclosure can include a system 10 configured to provide an electric waveform for neural stimulation or nerve block. For example, the electrical waveform can be a charge-balanced, self-oscillating, voltage-boosted electric waveform. The voltage boosting capabilities of system 10 can allow system 10 to be incorporated into a waveform generator that can be part of an implantable neural stimulator. The implantable neural stimulator can be used within a neural prosthesis device. The system 10 can be powered by a small battery within the implantable device, and the battery can exhibit an extended life between battery changes. In some instances, system 10 can receive power temporarily by a capacitance substituting for a battery.

The system 10 can include components including at least an oscillating circuit component 12 and a balancing circuit component 14. The oscillating circuit component 12 can be configured to provide a self-oscillating, voltage-boosted electric waveform (EW) to the balancing circuit component 14. For example, the oscillating circuit can be configured to utilize Lenz's law to facilitate an amplification of a supply voltage from a battery to provide the self-oscillating, voltage-boosted electric waveform (EW).

Figure 2:
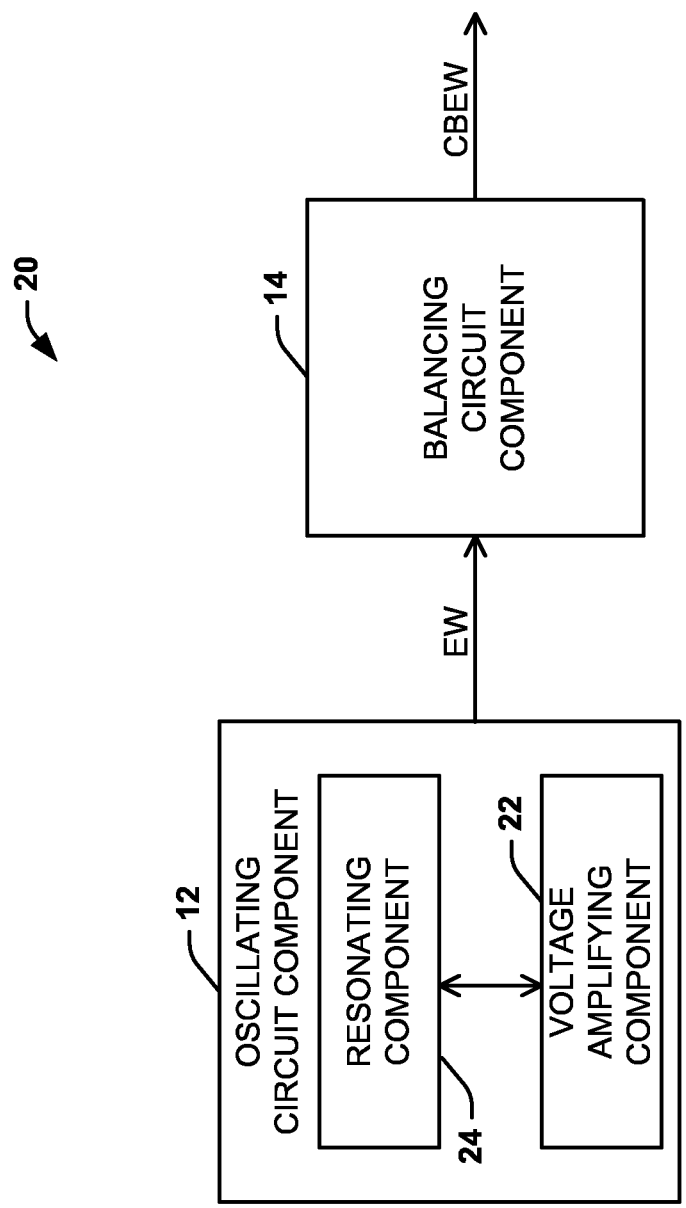
FIG. 2 is a schematic block diagram showing an example of an oscillating circuit component that can be used in the system shown in FIG. 1.

In some instances (e.g., as shown in FIG. 2), the oscillating circuit component can include a voltage amplifying component 22 and a resonating component 24. The voltage amplifying component 22 can be is configured to generate voltage pulses that are amplified from a supply voltage from a battery. In some instances, the voltage-amplifying circuit can include one or more of: a diode, a relay, a transistor, and an inductor (e.g., provided by a toroid, a transformer, or a multi-coil inductor). For example, the voltage-amplifying component 22 can include a circuit based on a joule thief circuit, a joule ringer circuit, and/or a fly-back transformer circuit.

The resonating component 24 can be configured to generate a self-oscillating signal. In some instances, the resonating component 24 can include at least one inductor (e.g., provided by a toroid, a transformer, or a multi-coil inductor) and at least one capacitor to form an LC resonating circuit. The LC resonating circuit can include other circuit elements (e.g., one or more resistors).

Referring again to FIG. 1, the balancing circuit component 14 can be configured to ensure that the self-oscillating, voltage boosted electric waveform is charged balanced. In some instances, the balancing circuit component 14 can be configured to remove contaminating noise from the self-oscillating, voltage-boosted electric waveform (EW) to facilitate the charge balancing.

The system 10 can output the charge-balanced, self-oscillating, voltage-boosted electric waveform (CBEW). In some instances, the output can be current controlled. In other instances, the output can be voltage controlled.

Figure 3:
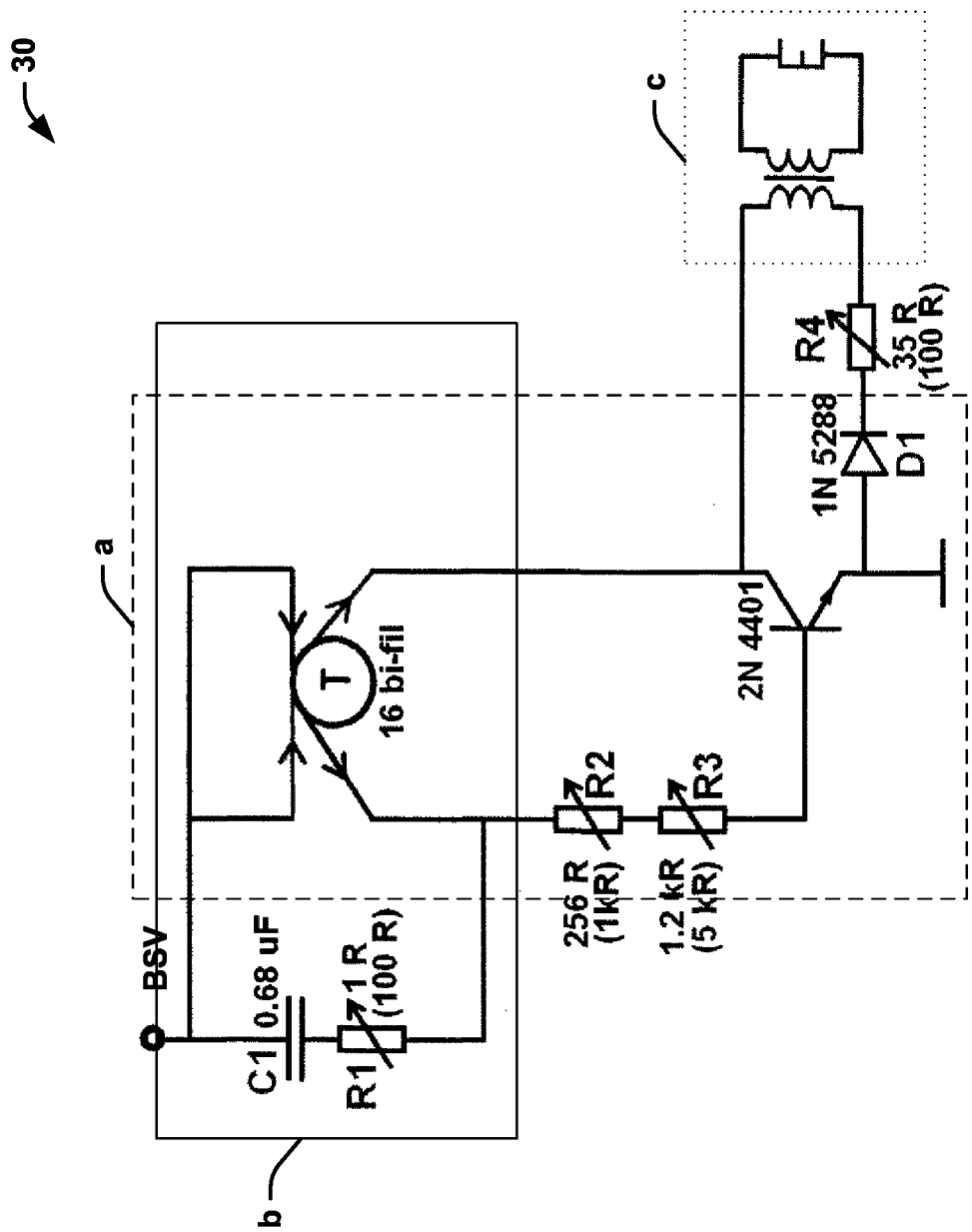
FIG. 3 is a diagram of an example circuit configuration of the system shown in FIG. 1.

One example implementation of the system 10 is shown in the circuit diagram 30 of FIG. 3. For example, the oscillating circuit component 12 of system 10 can include elements a (e.g., voltage amplifying component 22 of FIG. 2) and b (e.g., resonating component 24 of FIG. 2) of the circuit diagram 30 and the balancing circuit component 14 can include element c of the circuit diagram 30. As depicted in circuit diagram 30, element a can be based on a joule-thief circuit, a joule-ringer circuit or a fly-back transformer circuit, element b can be a resonating RC-circuit (e.g., that can "round" the waveform), and element c can be a transformer that can balance the charge in the output waveform.

Figure 4:
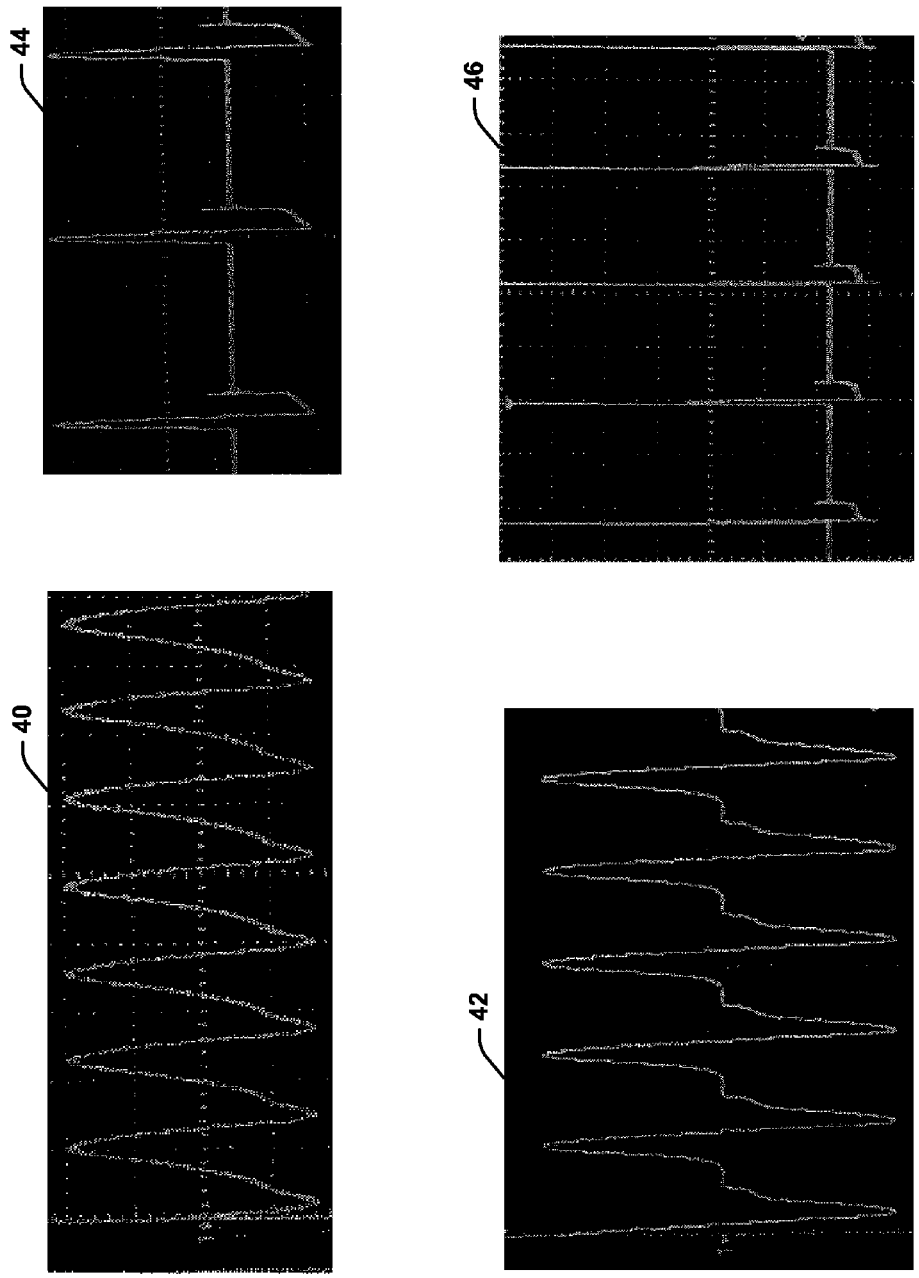
FIG. 4 shows example waveforms that can be produced by the circuit shown in FIG. 3.

Examples of different outputs that can be output from circuit illustrated in circuit diagram 30 are shown in FIG. 4. Each plot 40, 42, 44, and 46 is biphasic and charge-balanced. Moreover, each plot 40, 42, 44, and 46 is self-oscillating and voltage-boosted. The different plots 40, 42, 44, and 46 are generated by altering the circuit components in different ways.

The circuit components of the circuit in circuit diagram 30 can be altered to change the form (e.g., parameters) of the output. In some instances, the output can be fixed in waveform shape, pulse-width, cathodic and anodic amplitudes, and frequency. For example, the waveform shape can be varied by one or more of: the choice of resistors, the choice of diode (D1), the choice of inductor/toroid/number of windings, and the capacitor (C1) in direct connection to the toroid. As another example, the fundamental frequency can be varied by one of more of: choice of diode (D1), choice of capacitor (C1) and resistor (R1), choice of resistors (R2, R3, and/or R4), and choice of inductor/toroid/number of windings. In a further example, the pulse width can be varied by one or more of: choice of capacitor (C1) and resistor (R1), choice of resistors (R2, R3, and/or R4), and choice of inductor/toroid/number of windings. In yet another example, the on-time/off-time of the output can be varied by one or more of: choice of the diode (D1) and choice of resistor (R3).

Figure 5:
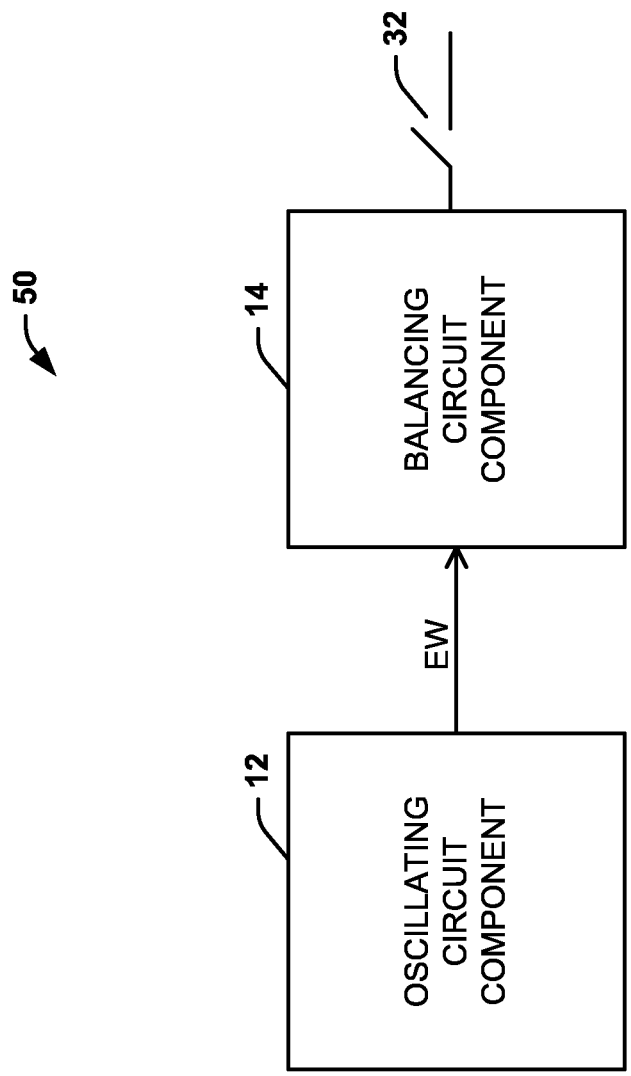
FIGS. 5 and 6 are schematic block diagrams showing example placements of a trigger switch into the system shown in FIG. 1.
Figure 6:
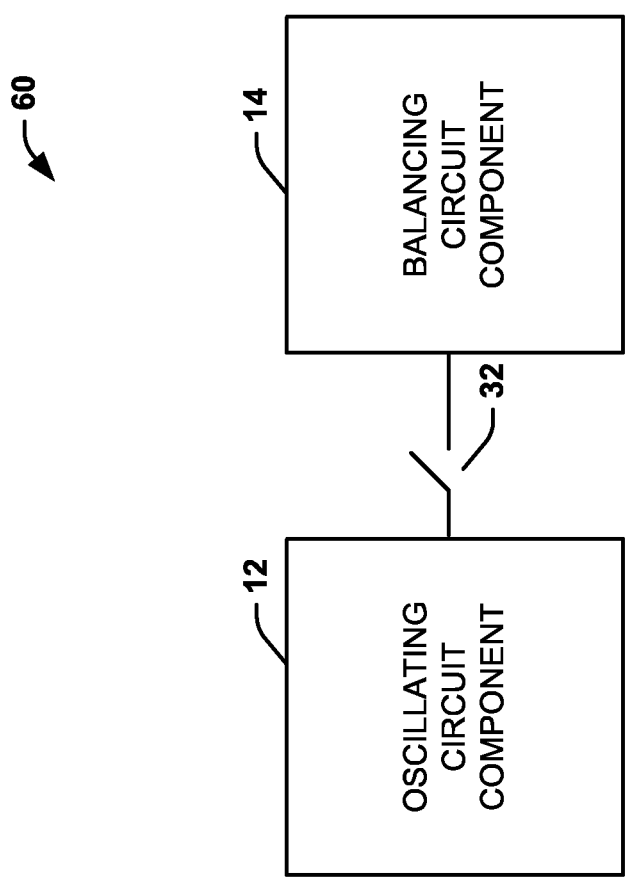

As shown in FIGS. 5 and 6, systems 50 and 60 (respectively) can include a trigger switch 32 that can be configured to interrupt transmission of the electric waveform (EW). The trigger switch 32 can be located within the oscillating circuit component 12, between the oscillating circuit component and the balancing circuit component 14, within the balancing circuit component, or at the output of the system 10. When the trigger switch 32 is in an open configuration, an open circuit can be created through at least one path of the oscillating circuit component 12 or the balancing circuit component 14.

Figure 7:
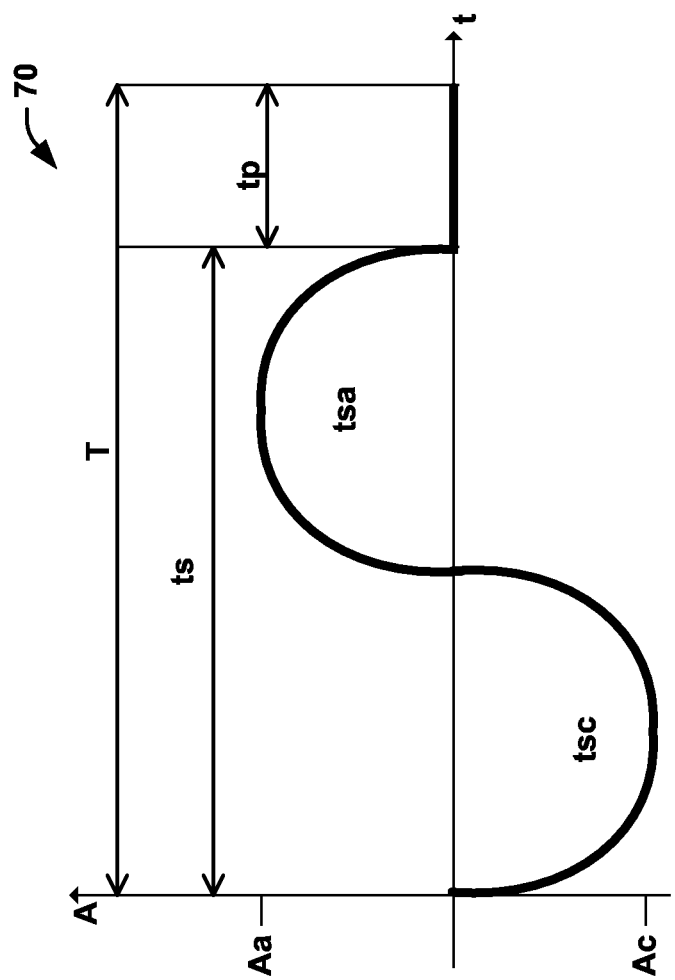
FIG. 7-9 are a schematic illustrations of waveforms that can be produced by the systems shown in FIGS. 5 and 6.

In some instances, the trigger switch 32 can be operated by the oscillating circuit component 12 to short circuit transmission of the electric waveform in at least one of the oscillating circuit component 12 or the balancing circuit component 14 to provide a zero-amplitude waveform as an output of the system 50 at one or more time points ("pause time"). An example of a waveform 70 with a biphasic portion and an interrupted portion is shown in FIG. 7. The biphasic portion can have a cathodic phase and an anodic phase (in either order). As illustrated, the cathodic phase occurs over a first time period (tsc), and the anodic phase occurs over a second time period (tsa). The sum of the first time period and the second time period can be defined as the swing time (ts) of the biphasic waveform (or ts=tsc+tsa). The interrupted portion can occur over a pause time (tp) where the waveform can have a substantially constant amplitude. The period of the entire waveform 70 (T) can be defined as the sum of the swing time and the pause time (T=ts+tp). The biphasic waveform can be charge-balanced during the time period (T).

In some instances, the pause waveform can be provided by a waveform generator. For example, the waveform generator can include a trigger switch that can create an open circuit with the waveform generator (e.g., shorting one or both lines of a channel of the waveform generator) to discharge contaminating noise (e.g., a direct current (DC) component). In another example, the trigger switch can create an open circuit within the waveform generator to interrupt the biphasic waveform for the pulse time. In another example, the waveform generator can be the system 50 or 60 where the trigger switch 32 can be configured to interrupt the output of the self-oscillating, voltage-boosted electric waveform for the pause time interval upon completion of at least one cathodic phase and/or at least one anodic phase.

During the pause time, the waveform can have a substantially constant amplitude. For example, the substantially constant amplitude can be provided to one or more output terminals of the waveform generator during the pause time. Different examples of waveforms with pause times are shown in FIGS. 8 and 9.

Figure 8:
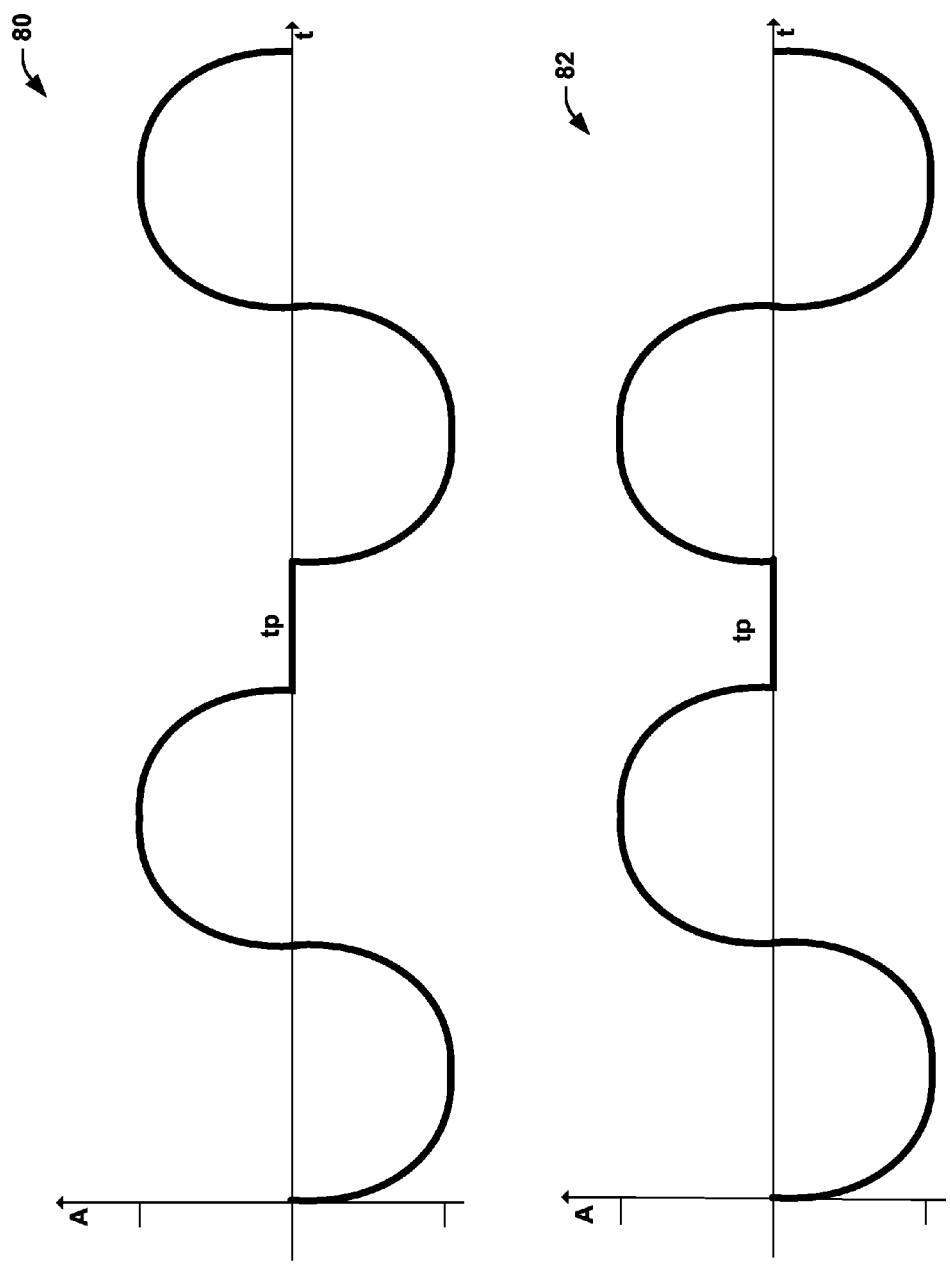

In FIG. 8 elements 80 and 82 show a substantially constant amplitude of zero Amps during the pause time (the amplitude could alternatively be zero Volts). Element 80 illustrates the same polarity biphasic waveform before and after the pause time. Element 82 illustrates different polarities of the biphasic waveform (e.g., a reversed polarity) before and after the pause time. In some instances, reversing the polarity of the waveform can provide charge balancing of the overall waveform over two or more periods (T).

Figure 9:
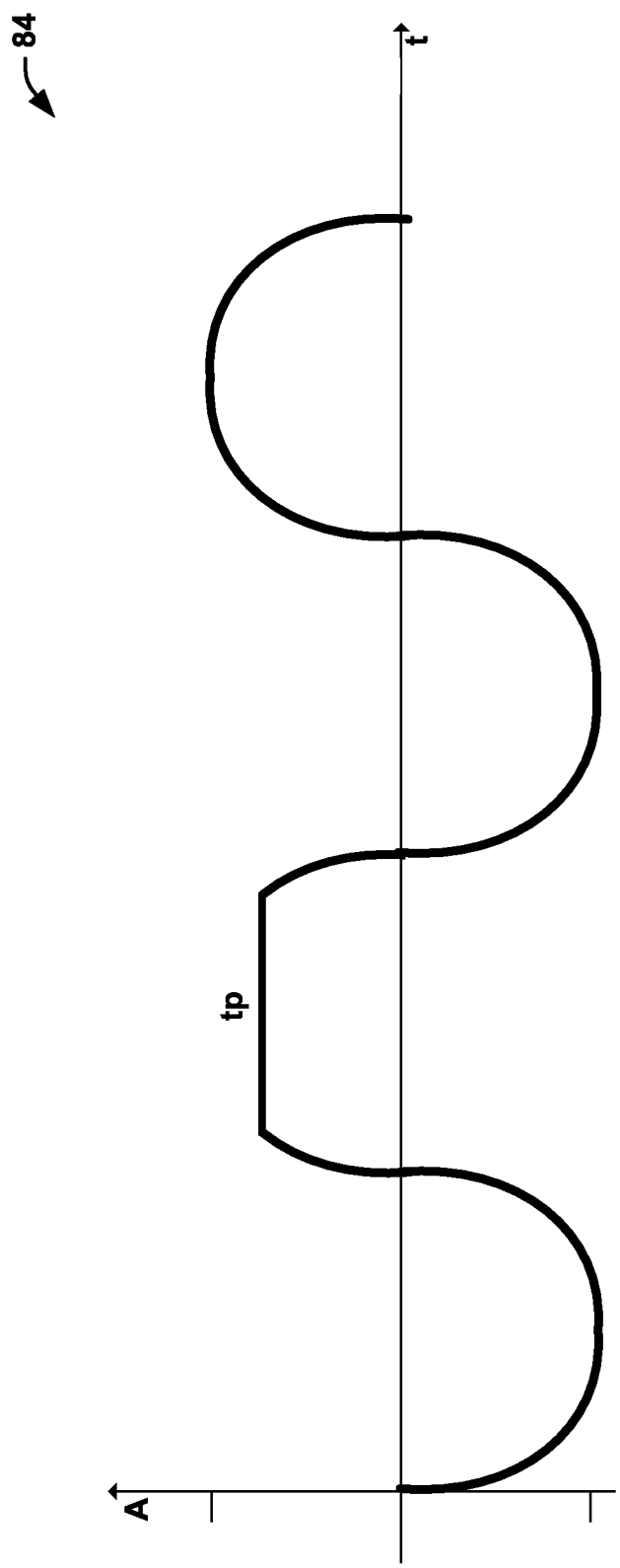

In FIG. 9, element 84 shows a substantially constant amplitude that is non-zero Amps (the amplitude could alternatively be a non-zero value in Volts). In some instances, during the non-zero amplitude pause time, the waveform generator can send and/or receive data with a reduction in noise.

It will be understood that the "waveform generator" or "waveform generation device" as used herein can be any device that can generate a biphasic waveform. In some instances, the waveform generator or waveform generation device can include one or more components of system 10, system 20, system 50 or system 60.

IV. Methods

Figure 10:
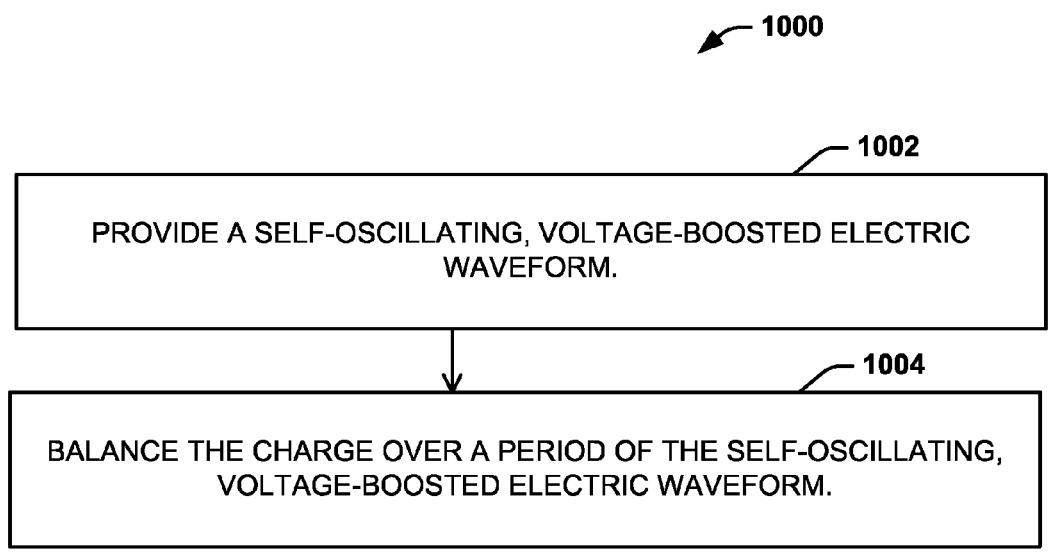
FIG. 10 is a process flow diagram illustrating a method for providing an electric waveform for neural stimulation or nerve block in accordance with another aspect of the present disclosure.

Another aspect of the present disclosure can include methods that can provide a waveform for neural stimulation or nerve block, according to an aspect of the present disclosure. An example of a method 1000 that can provide an electric waveform (e.g., as shown in FIG. 4) for neural stimulation or nerve block is shown in FIG. 10. Another example of a method 1100 that can interrupt an electrical waveform (e.g., as provided by method 1000) to form a pause waveform (e.g., as show in FIGS. 7-9) is shown in FIG. 11.

Figure 11:
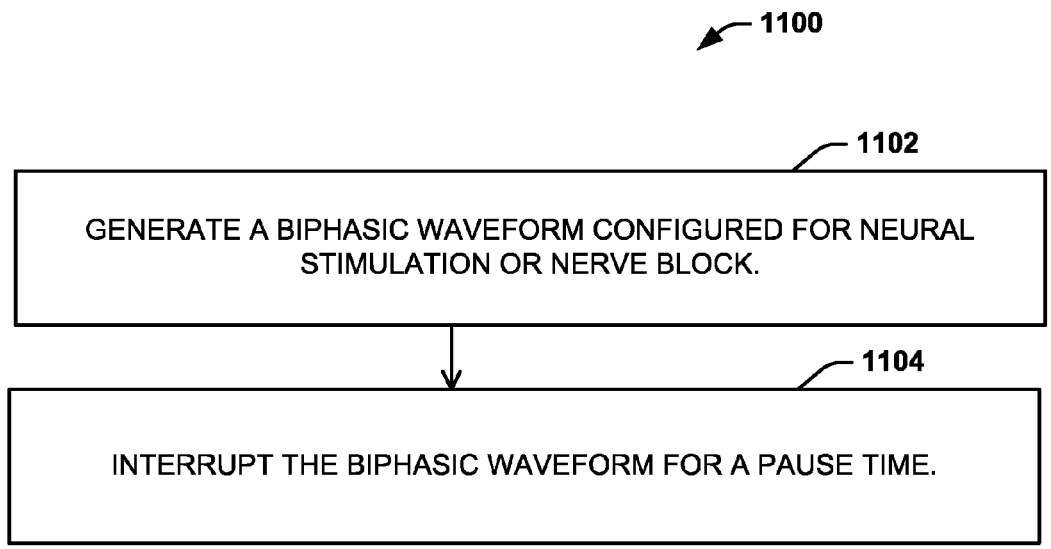
FIG. 11 is a process flow diagram illustrating a method for interrupting the electric waveform provided according to the method shown in FIG. 10.

The methods 1000 and 1100 of FIGS. 10 and 11, respectively, are illustrated as process flow diagrams with flowchart illustrations. For purposes of simplicity, the methods 1000 and 1100 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 1000 and 1100.

Referring to FIG. 10, an aspect of the present disclosure can include a method 1000 for providing an electrical waveform (e.g., as shown in FIG. 4) for neural stimulation or nerve block. In some instances, the method 1000 can be accomplished by a waveform generation device. For example, the waveform generation device can be an implantable neural stimulator that can be used in connection with a neural prosthetic device.

At 1002, a self-oscillating, voltage-boosted electric waveform (e.g., EW) can be provided (e.g., by oscillating circuit component 12). For example, the self-oscillating, voltage-boosted electric waveform can be generated according to Lenz's law to facilitate an amplification of a supply voltage from a battery.

At 1004, the charge during a period of the self-oscillating, voltage-boosted waveform can be balanced (e.g., by balancing circuit component 14). The charge-balanced, self-oscillating, voltage-boosted waveform can be an output of a system implementing the method. In some instances, the output can be current-controlled. In other instances, the output can be voltage controlled.

In some instances, during the charge-balancing, any contaminating noise (e.g., direct current (DC) components) in the self-oscillating, voltage-boosted electric waveform can be removed. By removing the contaminating noise, the charge-balanced, self-oscillating, voltage-boosted waveform can be safer for the neural stimulation or nerve block (e.g., the waveform will be less likely to damage the nerve, the electrode applying the waveform, and/or the waveform generator).

Referring now to FIG. 11, another aspect of the present disclosure can include a method 1100 for interrupting an electrical waveform (e.g., as provided by method 1000) to form a pause waveform (e.g., as show in FIGS. 7-9).

At 1102, a biphasic waveform (e.g., as shown in FIG. 4) configured for neural stimulation or nerve block can be generated. In some instances, the biphasic waveform can be generated by a waveform generation device (e.g., at least a portion of the systems 10 or 20 as shown in FIG. 1 or 2). For example, the biphasic waveform can be an electrical waveform that can be generated by steps 1002 (in which a self-oscillating, voltage-boosted electric waveform (e.g., EW) can be provided (e.g., by oscillating circuit component 12)) and 1004 (in which the charge during a period of the self-oscillating, voltage-boosted waveform can be balanced (e.g., by balancing circuit component 14)) of FIG. 10.

At 1104, the biphasic waveform can be interrupted (e.g., by a trigger switch 32 creating an open circuit within the waveform generator to short out the output internally and by shorting one or more lines of a channel of the waveform generator) during the pause time to discharge contaminating noise (e.g., example waveforms with pause times ("pause waveforms") are shown in FIGS. 7-9). The interrupted waveform can have a substantially constant amplitude. In some instances, the amplitude can be about zero Volts or zero Amps. In other instances, the amplitude can be a non-zero value of voltage or current.

For example, the biphasic waveform and the interrupted waveform together can have a period (T) that is equal to the sum of a swing time (ts) and a pause time (tp). In some instances the swing time (ts) can include the time to complete both phases of the biphasic waveform. In other instances, the swing time (ts) can include a time to complete a single phase of the biphasic waveform. The pause time can stop the biphasic waveform at a high level (e.g., the maximum amplitude of the biphasic waveform), at an intermediate level (e.g., between zero and the maximum amplitude of the biphasic waveform), or at an amplitude of zero.

In some instances, the biphasic waveform can be charge-balanced during the time period (T). For example, unbalanced charge (e.g., due to contaminating DC noise) can be discharged during the pause time.

From the above description, those skilled in the art will perceive improvements, changes and modifications. Such improvements, changes and modifications are within the skill of one in the art and are intended to be covered by the appended claims.

What is claimed is:

1. A system that provides an electric waveform for neural stimulation or nerve block, the system comprising:
   a first circuit component configured to provide a self-oscillating, voltage-boosted electric waveform; and
   a second circuit component configured to ensure that the self-oscillating, voltage-boosted electric waveform is charge-balanced across at least one period of the a self-oscillating, voltage-boosted electric waveform;
   wherein an output of the system comprises the charge-balanced self-oscillating, voltage-boosted waveform;
   wherein the second circuit component is configured to ensure that the output of the system is free of contaminating direct current (DC) components.

2. The system of claim 1, wherein the first circuit component is configured to utilize Lenz's law to facilitate an amplification of a supply voltage from a battery to provide the self-oscillating, voltage-boosted electric waveform.

3. The system of claim 1, wherein the output of the system is current controlled.

4. The system of claim 1, where in the output of the system is voltage controlled.

5. The system of claim 1, wherein the first circuit component comprises a resonating circuit comprising at least one inductor and at least one capacitor.

6. The system of claim 5, wherein the first circuit component further comprises at least one resistor.

7. The system of claim 5, wherein the at least one inductor is provided by a tor aid, a transformer, or a multi-coil inductor.

8. The system of claim 5, wherein the first circuit component further comprises at least one of a transistor, a diode, and a relay.

9. The system of claim 1, further comprising a trigger switch configured to interrupt transmission of the electric waveform through at least one path of the first circuit component or the second circuit component.

10. The system of claim 9, wherein the trigger switch is at least one of:
    located between the first circuit component and the second circuit component; and
    located within the second circuit component.

11. The system of claim 9, wherein the trigger switch is operated by the first circuit component and configured to short-circuit the electric waveform in at least one of the first circuit component and the second circuit component to provide a zero-amplitude waveform as an output of the system at a plurality of time points.

\* \* \* \* \*